US006661161B1

(12) United States Patent
Lanzo et al.

(10) Patent No.: US 6,661,161 B1
(45) Date of Patent: Dec. 9, 2003

(54) PIEZOELECTRIC BIOLOGICAL SOUND MONITOR WITH PRINTED CIRCUIT BOARD

(75) Inventors: Vittorio F. Lanzo, Laval (CA); Van Con Nguyen, Montréal (CA); George Cybulski, Beaconsfield (CA); Larrimore A. S. Adams, Lachine (CA)

(73) Assignee: Andromed Inc., St-Laurent (CA)

( * ) Notice: Subject to any disclaimer, the term of this patent is extended or adjusted under 35 U.S.C. 154(b) by 0 days.

(21) Appl. No.: 10/180,518

(22) Filed: Jun. 27, 2002

(51) Int. Cl.[7] .............................................. H02K 11/08
(52) U.S. Cl. ...................................................... 310/334
(58) Field of Search ................................ 310/334, 324, 310/340, 344

(56) References Cited

U.S. PATENT DOCUMENTS

| | | | | |
|---|---|---|---|---|
| 3,682,161 A | * 8/1972 | Alibert | 310/334 |
| 4,127,749 A | * 11/1978 | Atoji et al. | 310/800 |
| 4,326,143 A | 4/1982 | Guth et al. | |
| 4,884,809 A | * 12/1989 | Rowan | 463/47.3 |
| 5,033,032 A | 7/1991 | Houghtaling | |
| 6,486,588 B2 | * 11/2002 | Doron et al. | 310/322 |

FOREIGN PATENT DOCUMENTS

| | | |
|---|---|---|
| EP | 0 716 628 B1 | 2/1998 |
| EP | 0 659 058 B1 | 1/1999 |
| WO | WO 94/13207 | 6/1994 |
| WO | WO 99/53277 | 10/1999 |
| WO | WO 00/10462 | 3/2000 |
| WO | WO 01/34033 A1 | 5/2001 |
| WO | WO 01/97691 A1 | 12/2001 |
| WO | WO 02/03042 A1 | 1/2002 |

* cited by examiner

*Primary Examiner*—Thomas M. Dougherty
*Assistant Examiner*—Karen Addison
(74) *Attorney, Agent, or Firm*—Birch, Stewart, Kolasch & Birch, LLP

(57) ABSTRACT

The piezoelectric sound monitor comprises a piezoelectric membrane including an inner face, an outer face, and first and second peripheral portions. The piezoelectric sound monitor further comprises a piezoelectric membrane support structure including an outer face, two first mutually facing membrane-clamping walls, a first electrically conductive area, two second mutually facing membrane-clamping walls, and a second electrically conductive area. The inner face of the piezoelectric membrane is applied to the outer face of the support structure. The first peripheral portion of the piezoelectric membrane is clamped between the two first walls, and the first electrically conductive area is located on one of the two first walls for electrically contacting the inner face of the piezoelectric membrane. The second peripheral portion of the piezoelectric membrane is clamped between the two second walls, and the second electrically conductive area is located on one of the two second walls for electrically contacting the outer face of the piezoelectric membrane.

21 Claims, 7 Drawing Sheets

26
13
4
30
20
24
16
18
2
6
22
28
103
40
38
32
60
8
55
48
34
52
53
92
61
10
65
63

56
60
2
IV
IV

PIEZOELECTRIC BIOLOGICAL SOUND MONITOR WITH PRINTED CIRCUIT BOARD

FIELD OF THE INVENTION

The present invention relates to a piezoelectric sound monitor capable of converting acoustic waves to an electric signal.

BACKGROUND OF THE INVENTION

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including:

- a wide frequency range of between 0.001 Hz to 1 GHz;
- a low acoustical impedance close to water and human tissue;
- a high dielectric strength;
- a good mechanical strength; and
- piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. In this regard, sound detecting devices have used piezoelectric membranes as mechano-electric transducers where the piezoelectric membrane becomes temporarily polarised when subjected to a physical force with the direction and the magnitude of the polarisation depending on the magnitude of the force applied.

EPO Patent No. EP 0 716 628 granted to Kassal et al. on Dec. 2, 1998 discloses a disposable acoustic pad sensor including a piezoelectric membrane bonded to a flexible substrate for the detection of heart sounds. The sensor is applied to a patient's skin with an adhesive or electrode cream and flexes with heartbeat. Similarly, PCT application to Gavrieli et al., published on Oct. 21, 1999 under number WO 99/53277 discloses a device for detecting sounds generated within a patient's body comprising a piezoelectric sensor placed on the surface of the body and an electronic circuitry for rejecting airborne sounds such as speech. The piezoelectric material in both these sensor and device is typically bonded to a semi-rigid substrate with flexing of the substrate being sensed via the piezoelectric material.

Sensors have also been developed for detecting body sounds where amplification and other signal processing electronics are located within the sensor and/or proximate to the sensor. PCT application (Smith) published on May $17^{th}$, 2001 under number WO 01/34033 discloses a stethoscope transducer comprising a diaphragm and co-located signal amplification and filtering electronics. Similarly, PCT application (Sullivan et al.) published on Dec. $27^{th}$, 2001 under number WO 01/97691 discloses a biophysical sensor comprised of a piezoelectric membrane and signal amplification and filtering electronics encapsulated in a single package.

SUMMARY OF THE INVENTION

The present invention relates to a piezoelectric sound monitor comprising piezoelectric membrane including an inner face, an outer face, and first and second peripheral portion. The piezoelectric sound monitor also comprises a piezoelectric membrane support structure including an outer face, two first mutually facing membrane-clamping walls, a first electrically conductive area, two second mutually facing membrane-clamping walls, and a second electrically conductive area. The inner face of the piezoelectric membrane is applied to the outer face of the support structure. The first peripheral portion of the piezoelectric membrane is clamped between the two first walls, and the first electrically conductive area is located on one of the two first walls for electrically contacting the inner face of the piezoelectric membrane. The second peripheral portion of the piezoelectric membrane is clamped between the two second walls, and the second electrically conductive area is located on one of the two second walls for electrically contacting the outer face of the piezoelectric membrane.

The present invention also relates to a piezoelectric sound monitor, comprising:

- a frame defining a window and having first and second faces;
- a piezoelectric membrane extending across the window of the frame and including an outer face, an inner face applied to the first face of the frame, and first and second generally opposite peripheral portions;
- a board having a first face toward the second face of the frame, a second face opposite to the first face, a first electrically conductive area on the first face of the board, and a second electrically conductive area on the second face of the board; and
- a housing connected to the frame and having an inner face toward the second face of the board.

The first peripheral portion of the piezoelectric membrane is bent over the second face of the frame and clamped between the second face of the frame and the first electrically conductive area whereby the first electrically conductive area is in electrical contact with the outer face of the piezoelectric membrane.

In the same manner, the second peripheral portion of the piezoelectric membrane is bent over the second face of the board and is clamped between the second electrically conductive area and the inner face of the housing whereby the second electrically conductive area is in electrical contact with the inner face of the piezoelectric membrane.

The present invention is further concerned with a method for fabricating a sound monitor for the detection of sounds, comprising:

- clamping a first peripheral portion of a piezoelectric membrane to a first contact area such that a first face of the piezoelectric membrane is in contact with the first contact area;
- spreading the piezoelectric membrane across a window of a frame; and clamping a second peripheral portion of the piezoelectric membrane to a second contact area such that a second surface of the piezoelectric membrane is in contact with the second contact area.

The foregoing and other objects, advantages and features of the present invention will become more apparent upon reading of the following non restrictive description of illustrative embodiments thereof, given for the purpose of illustration only with reference to the accompanying drawings.

DETAILED DESCRIPTION OF THE ILLUSTRATIVE EMBODIMENTS

Illustrative embodiments of a piezoelectric, biological sound monitor according to the present invention will now be described with reference to the appended drawings. In the appended figures, the biological sound monitor is generally identified by the reference 2.

Those of ordinary skill in the art will appreciate that application of the piezoelectric sound monitor is not limited to detection of biological sounds.

Figure 1:
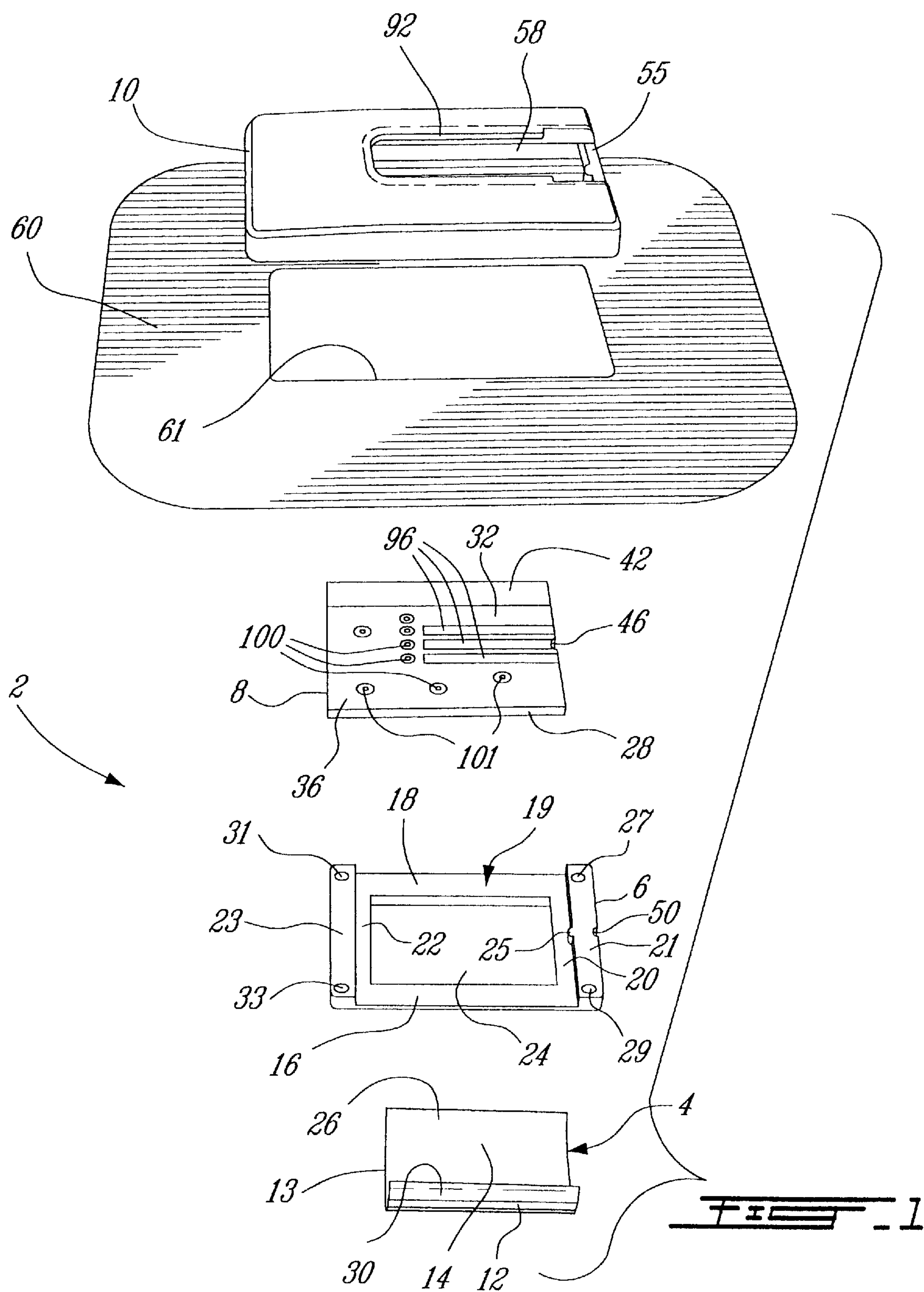
FIG. 1 is an exploded, top perpective view of an illustrative embodiment of a piezoelectric sound monitor according to the present invention.
Figure 2:
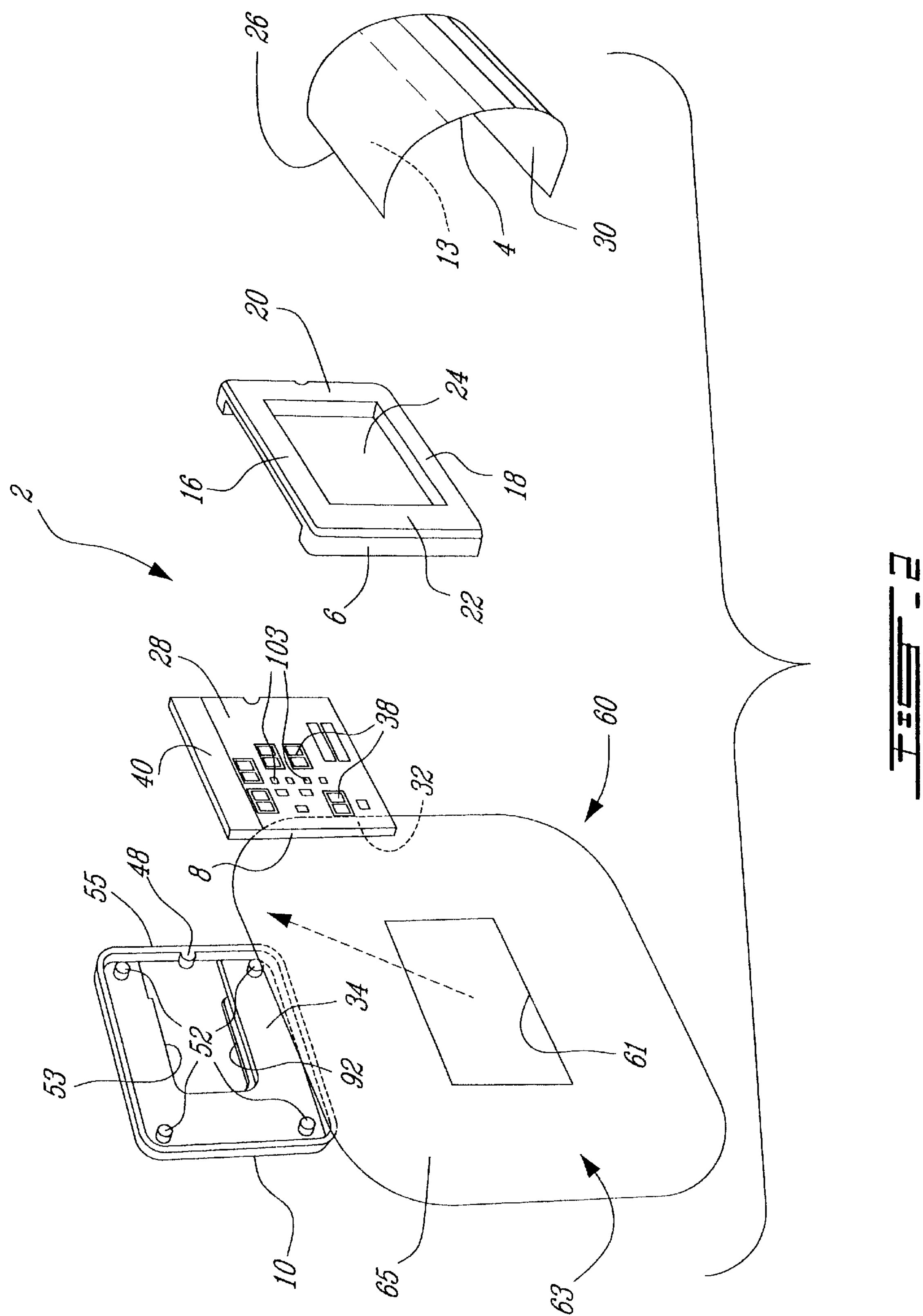
FIG. 2 is an exploded, bottom perspective view of the illustrative embodiment of piezoelectric sound monitor as shown in FIG. 1.

As illustrated in FIGS. 1 and 2, the biological sound monitor 2 comprises a rectangular piezoelectric membrane 4, a rectangular frame 6, a rectangular printed circuit board (PCB) 8, a self-adhesive pad 60, and a housing 10.

According to the illustrative embodiment of the biological sound monitor 2, the piezoelectric membrane 4 comprises a sheet 13 of piezoelectric material used as mechano-electrical transducer. In operation, the piezoelectric material becomes temporarily polarized when subjected to a mechanical stress and the direction and magnitude of the polarization depend upon the direction and magnitude of the mechanical stress. Therefore, the piezoelectric material of the sheet 13 will produce a voltage and current, or will modify the magnitude of a current flowing through it in response to a change in the mechanical stress applied thereto. In other words, the electrical charge generated by the piezoelectric material is proportional to the change in mechanical stress.

The piezoelectric membrane 4 further comprises a first electrode coating 12 applied to an outer face of the sheet 13 of piezoelectric material, and a second electrode coating 14 applied to an inner face of this sheet 13 of piezoelectric material. Detection of voltage and/or current through the piezoelectric material is obviously made through these first and second electrode coatings 12 and 14.

Accordingly, stresses produced by acoustic waves in the piezoelectric membrane 4 will produce a corresponding electric signal. Of course, detection of this electric signal requires connection of the first and second electrode coatings 12 and 14 to a detector circuit.

The rectangular frame 6 can be made of molded plastic material. Frame 6 defines a rectangular window 24 and an outer face. The piezoelectric membrane 4 is applied to the outer face of the frame 6 and is spread over the rectangular window 24. The rectangular frame 6 also defines, around the window 24, a pair of opposite longer members 16 and 18, and a pair of opposite shorter members 20 and 22. The rectangular frame 6 further comprises an inner face that is hollowed out to form a rectangular seat 19 for the PCB 8. The seat 19 is delimited at both ends of the rectangular frame 6 by non-hollowed-out portions 21 and 23 of the shorter members 20 and 22. As illustrated in FIG. 1, member portions 21 and 23 are longitudinal with respect to the member 20 and 22 but are transversal to the frame 6.

End portion 21 is formed with central and opposite inner boss 25 and outer notch 50. End portion 21 also comprises, through the inner face thereof, two opposite end cylindrical holes 27 and 29. In the same manner, end portion 23 is provided, through the inner face thereof, with two opposite end cylindrical holes 31 and 33.

Although a frame 6 of rectangular shape has been disclosed in the foregoing specification, it is within the scope of the present invention to use a frame having any other suitable shape or configuration.

The PCB 8 is rectangular to fit into the rectangular seat 19 of the frame 6 with the peg 25 fitting in a peripheral notch 46 of the PCB 8. PCB 8 presents a conventional structure including a non-conductive substrate 36 fabricated from plastic, non-conductive resin and/or other suitable material. The non-conductive substrate 36 is covered on both sides with a layer of electrically conductive material, usually metal such as aluminium, copper or tin-plated copper. The layers of electrically conductive material are then etched as required to provide an electrically conductive printed circuit for mounting electronic components (not shown) and/or conducting electrical signals.

Figure 3:
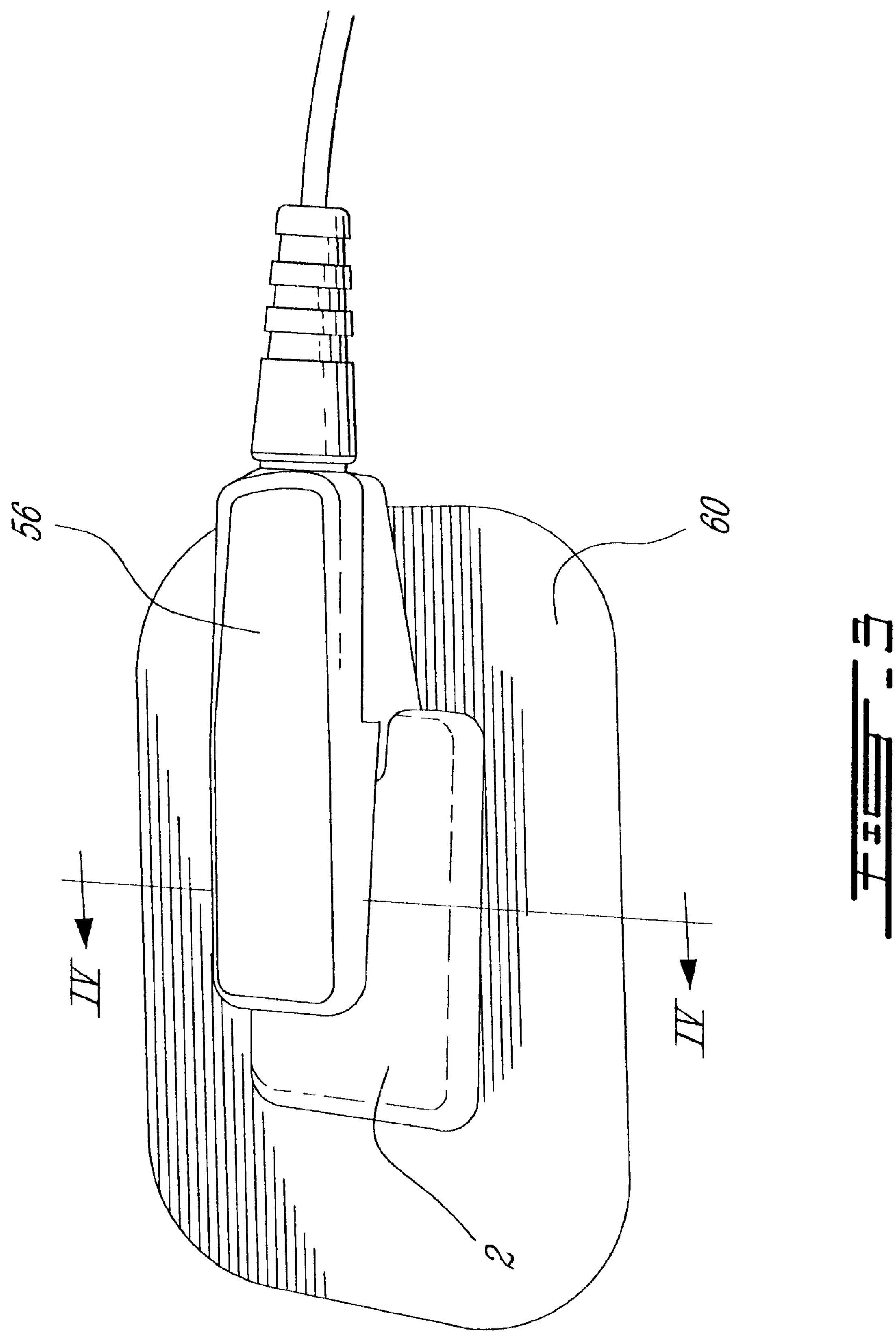
FIG. 3 is a top perspective view of the piezoelectric sound monitor of FIGS. 1 and 2, fully assembled and attached to an external connector according to an illustrative embodiment of the present invention.
Figure 4:
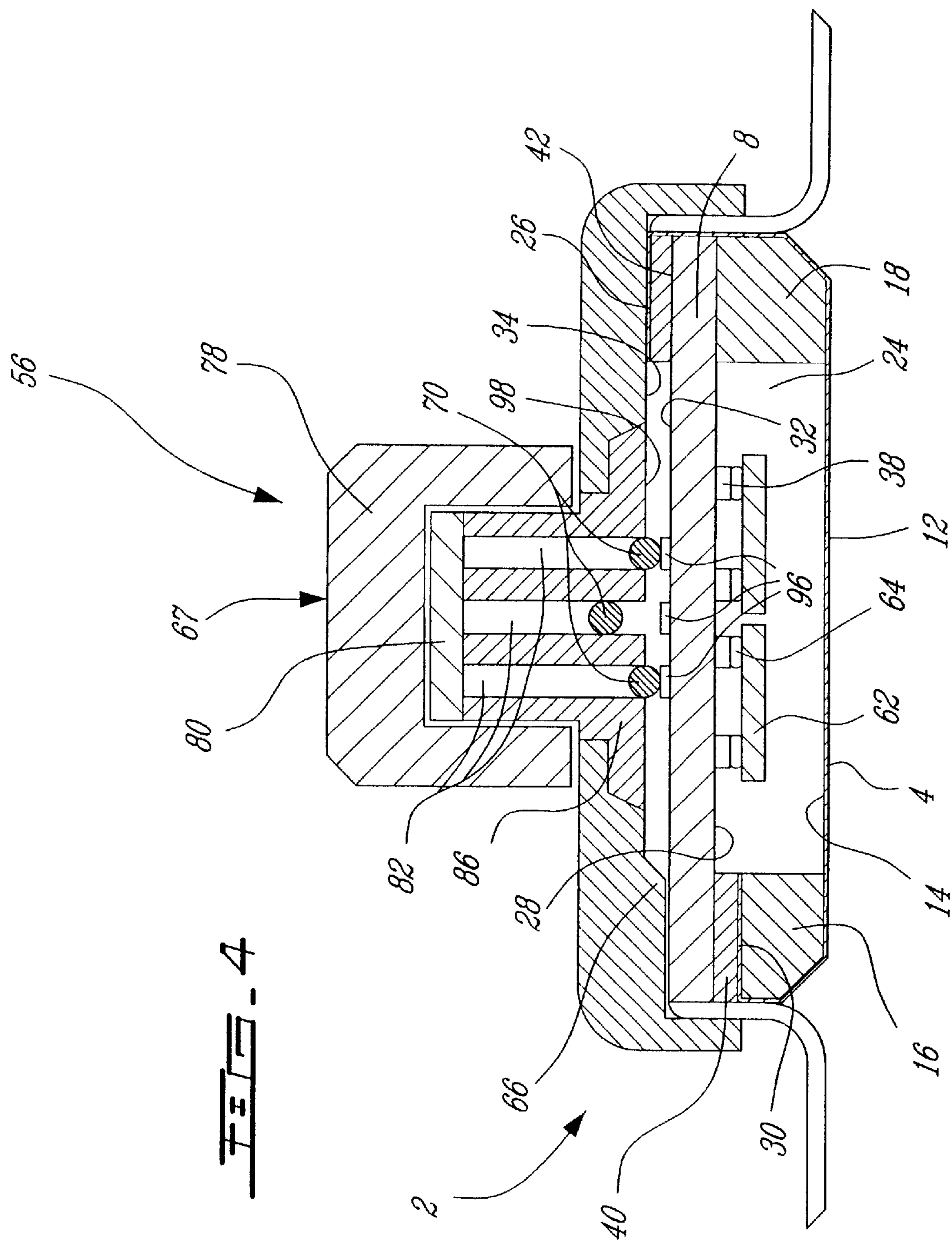
FIG. 4 is a cross-sectional view, taken along line IV—IV of FIG. 3, of the assembly including the piezoelectric sound monitor and external connector of FIG. 3.

The PCB 8 comprises:

on the top face of the PCB 8 (see FIG. 1):

- a longitudinal, electrically conductive exposed strip area 42 for connection to the inner face of the piezoelectric membrane 4, this strip area 42 being located adjacent to a first longitudinal edge of the rectangular substrate 36;
- three central, longitudinal, parallel, laterally adjacent and exposed electrically conductive traces 96 for connection to a connector 56 (FIGS. 3 and 4);

a plurality of perforations 100 machined through the substrate 36 between electrically conductive areas of the printed circuit on the top face of the PCB 8, and electrically conductive areas of the printed circuit on the bottom face of the PCB 8 to enable establishment of electrical connections between conductive areas respectively located on the top and bottom faces of the PCB 8;

exposed contact pads such as 101 forming part of respective electrically conductive areas of the printed circuit and surrounding respective perforations 100; and on the bottom face of the PCB 8 (see FIG. 2):

a longitudinal, electrically conductive exposed strip area 40 for connection to the outer face of the piezoelectric membrane 4, wherein strip area 40 is located on the bottom face of the substrate 36 adjacent a second longitudinal edge thereof opposite to the first longitudinal adjacent to strip area 42;

exposed contact pads such as 103 forming part of respective electrically conductive areas of the printed circuit and surrounding respective perforations 100; and a plurality of contact pads such as 38 for connecting and mounting electronic components to the PCB 8, these contact pads 38 being electrically connected to the printed circuit of the PCB 8.

A self-adhesive pad 60 comprises a perforation 61 through which the three laterally adjacent traces 96 will be exposed. Pad 60 has an area larger than the area of the biological sound monitor 2 and is typically made from a thin flexible non-conductive fibrous material. Pad 60 has a bottom face 63 covered with a suitable biocompatible adhesive. The adhesive is in turn covered by a peel-off protective backing 65 that can be easily removed immediately prior to applying the monitor 2 to a patient's skin.

The housing 10 can also be made of molded plastic material. The inner face of this housing 10 is formed with a rectangular shallow cavity 34 to fit the PCB 8 and frame 6 with the membrane 4 mounted on the frame 6 and the pad 60 clamped between the housing 10 and frame 6. Housing 10 further comprises a rectangular window 58 so positioned as to expose the three laterally adjacent traces 96.

The housing 10 further comprises:

four pins 52 respectively located in the four corners of the shallow cavity 34 for respective insertion in the holes 27, 29, 31 and 33 of the member portions 21 and 23 of the rectangular frame 6;

a U-shaped track 92 to receive the connector 56; and a bridge member 55 to define the window 58 at the corresponding end of the rectangular housing 10, this bridge member 55 being thinner than the housing 10 to enable sliding of the connector 56 in the U-shaped track 92.

In order to assemble the biological sound monitor 2, the inner face of the piezoelectric membrane 4 is applied to the outer face of the rectangular frame 6 and spread over the window 24.

The corresponding peripheral end portion 30 of the rectangular piezoelectric membrane 4 is bent over the inner face of the frame member 16. The PCB 8 is then placed into the rectangular seat 19 with with the boss 25 fitted into the notch 46 to laterally position the PCB 8 in the rectangular seat 19. The longitudinal, electrically conductive exposed strip area 40 is then in electrical contact with electrode coating 12 of the piezoelectric membrane 4.

Referring to FIG. 4, longer frame member 18 is thicker than longer frame member 16. This compensates for the additional thickness added to the frame member 16 by the end portion 30 of the piezoelectric membrane 4 and the electrically conductive strip area 40 of the PCB 8 to thereby maintain the faces of the PCB 8 substantially parallel to the faces of the piezoelectric membrane 4.

The corresponding peripheral end portion 26 of the piezoelectric membrane 4 is then bent over the longitudinal, electrically conductive exposed strip area 42. Strip area 42 is then in electrical contact with electrode coating 14 of the piezoelectric membrane.

The self-adhesive pad 60 is applied to the frame 6, PCB 8 and membrane 4, with the three laterally adjacent traces 96 exposed through the perforation 61. Of course, the self-adhesive bottom face 63 is on the side of the PCB 8.

Finally, the four pins 52 of the rectangular housing 10 are driven into the respective holes 27, 29, 31 and 33 of the member portions 21 and 23 of the rectangular frame 6 through the self-adhesive pad 60. During this operation, a central inner boss 48 of the bridge member 55 is inserted in notch 50 of the rectangular frame 6 in order to center the traces 96 in the rectangular window 58 of the housing 10, since the PCB 8 has already its notch 28 fitted with the boss 25. Also during this operation, the pad 60 is pierced by the pins 52 to reach the respective holes 27, 29, 31 and 33, thereby firmly securing pad 60 to the sound monitor 2. The diameters of the pins 52 and holes 27, 29, 31 and 33 are so selected that, after insertion, the pins 52 are secured in the respective holes to complete assembly of the biological sound monitor 2. To better secure the rectangular frame 6 to the housing 10, a suitable adhesive (not shown) could also be applied to the corner pins 52 prior to insertion thereof in the respective holes 27, 29, 31 and 33. The three laterally adjacent traces 96 are then exposed through the perforation 61 of the self-adhesive pad 60, and the rectangular window 58 of the housing 10.

After the biological sound monitor 2 has been assembled, the end portion 30 of the piezoelectric membrane 4 is clamped between the electrically conductive strip area 40 and the inner face of the frame member 16. In this manner, good electrical contact is established between the electrically conductive strip area 40 and the electrode coating 12. The electrically conductive strip area 40 is sufficiently large to provide adequate electrical contact with the electrode coating 12 of the membrane 4. Therefore, the electrically conductive strip area 40 serves the dual purpose of providing electrical contact with the electrode coating 12 and holding the end portion 30 of the piezoelectric membrane 4 spread over the window 24 of the rectangular frame 6.

In the same manner, the end portion 26 of the piezoelectric membrane 4 is clamped between the electrically conductive strip area 42 and the inner face of the shallow cavity 34 through the self-adhesive pad 60. In this manner, good electrical contact is established between the electrically conductive strip area 42 and the electrode coating 14 of the piezoelectric membrane 4. The electrically conductive strip area 42 is sufficiently large to provide adequate electrical contact with the electrode coating 14 of the membrane 4. Therefore, the electrically conductive strip area 42 serves the dual purpose of providing electrical contact with the electrode coating 14 and holding the piezoelectric membrane 4 spread over the window 24 of the rectangular frame 6.

As illustrated in FIG. 4, the shallow cavity 34 of the housing 10 includes a raised inner face section 66 to compensate for the additional thickness added to the top face 32 of the PCB 8 by the peripheral end portion 26 of the piezoelectric membrane 4 and the electrically conductive strip area 42 and thereby maintain the rectangular housing 10 substantially parallel to the piezoelectric membrane 4.

The self-adhesive pad sheet 60 is clamped between (a) the rectangular frame 6, the PCB 8 and the membrane 4 and (b) the rectangular housing 10. By removing the protective backing 65 the self-adhesive bottom face 63 of pad 60 can be adhered to the skin of a patient (not shown) with the outer face of the piezoelectric membrane 4 applied to the patient's skin. The biological sound monitor 2 is then capable of detecting sound coming from the inside of the patient's body.

As indicated in the foregoing description, the piezoelectric material of sheet core 13 becomes temporarily polarized when subjected to a mechanical stress caused by the acoustic waves coming from the inside of the patient's body. Accordingly, the piezoelectric membrane 4 will convert the acoustic waves from the inside of the patient's body to a corresponding electric signal. Of course, detection of this electric signal requires connection of the first and second electrode coatings 12 and 14 to a detector circuit.

Referring to FIG. 3 of the appended drawings, the external connector 56 is provided to electrically connect the biological sound monitor 2 to a external detector circuit(s) adapted to process the electric signal produced in response to the acoustic waves from the inside of the patient's body.

Referring now to FIG. 4 of the appended drawings, the electrically conductive strip areas 40 and 42 are electrically connected through the printed circuit of the PCB 8 and eventually through both the printed circuit and electronic components such as 62 of the PCB 8 to the three laterally adjacent electrically conductive traces 96. When required, soldering material is injected in the perforations 100 to interconnect the corresponding pairs of contact pads 101 and 103 and at the same time the corresponding electrically conductive areas and/or electronic components. The above mentioned electronic components such as 62 can be mounted on the contact pads such as 38 of the bottom face 28 of the PCB 8. These electronic components, when present, extend in the window 24 of the rectangular frame 6. In order to prevent them from impeding operation of the piezoelectric membrane 4 these electronic components such as 62 are typically low profile surface mounted devices (SMD) connected to the contact pads such as 38 using conventional soldering techniques, for example the flip-chip soldering technique. Flip-chip soldering uses small solder bumps such as 64 of predictable depth to ensure that the outer profile of the soldered components such as 62 is kept to a minimum.

Figure 5:
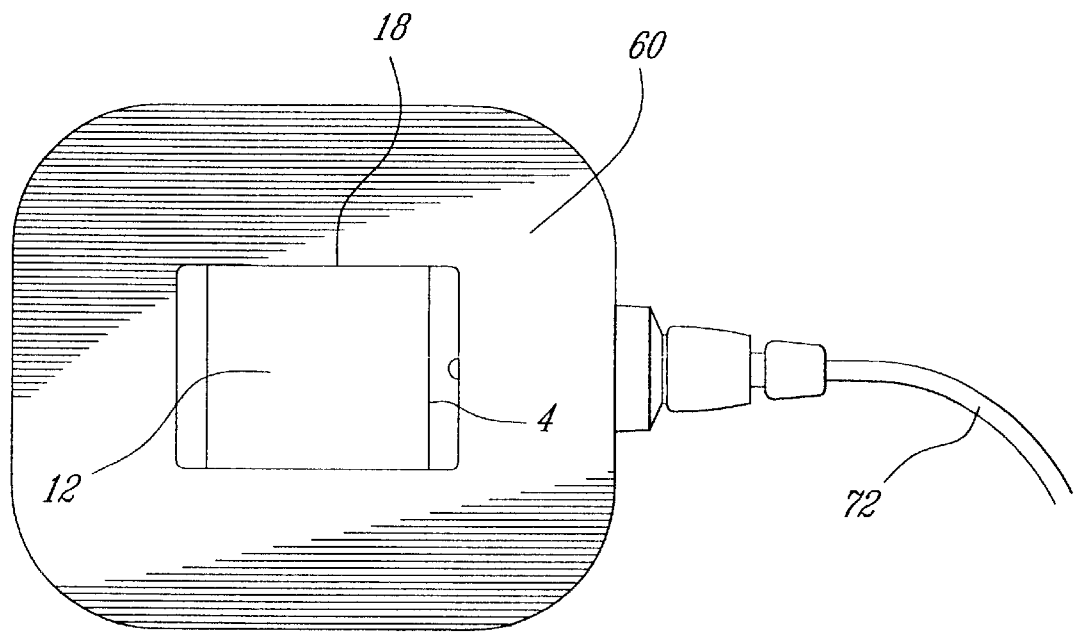
FIG. 5 is a bottom view of the assembly including the piezoelectric sound monitor and the external connector of FIG. 3.
Figure 6:
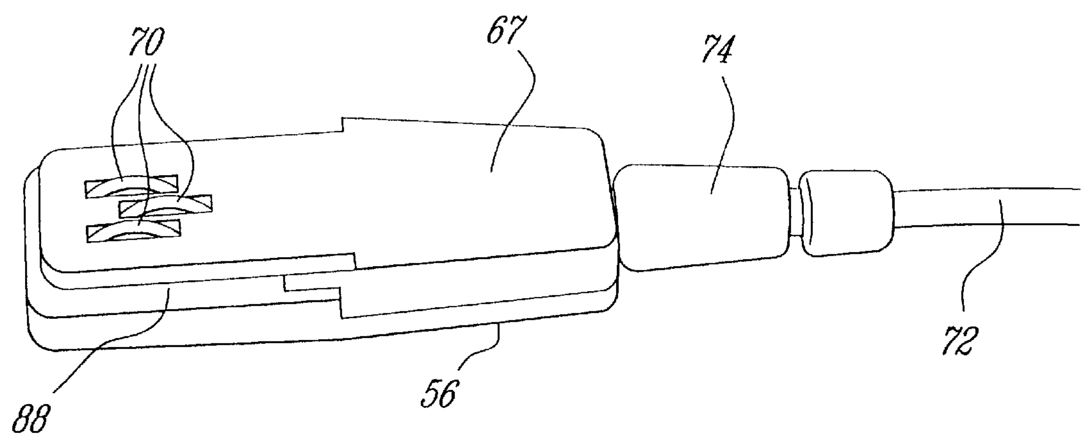
FIG. 6 is a bottom, perspective view of the external connector as shown in FIG. 3.

Electronic components such as 62 could include filters, amplifiers, etc. for pre-processing or processing the low amplitude electric signal from the piezoelectric membrane 4, prior to transmission thereof through the cable such as 72 in FIGS. 5 and 6 where it is susceptible of being greatly affected by interferences such as EMI interferences. It is within the scope of the present invention to mount on the contact pads such as 38 electronic components such as 62 capable of sophisticated processing of the electric signal. Such electronic components may include, for example, analog-to-digital converters for converting the electric signal to a digital signal and a central processing unit for analysing this digital signal.

It is also within the scope of the present invention to mount on the contact pads such as 38 a wireless transmitter for eliminating the need for connector 56 and cable 72. For example, optical transmission via at least one optic fibre or radio frequency (RF) transmission can be contemplated.

Figure 8:
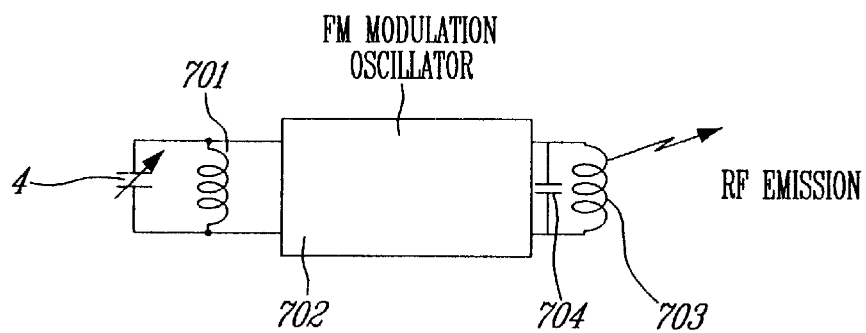
FIG. 8 is the circuit of an illustrative embodiment of piezoelectric sound monitor including a piezoelectric membrane, a FM modulation oscillator, and a RF emission circuit.

FIG. 8 is the circuit of a first group of electronic components that can be implemented on the PCB 8. The electric signal obtained from the piezoelectric membrane 4 is first filtered through an inductor 701 connected in parallel with membrane 4. The signal across the inductor 701 is applied to a FM (Frequency Modulation) modulation oscillator 702. Oscillator 702 frequency modulates the electric signal across inductor 701. The frequency-modulated signal from the oscillator 702 is supplied to an oscillator circuit (parallel inductor 703 and capacitor 704) for RF emission thereof.

Figure 9:
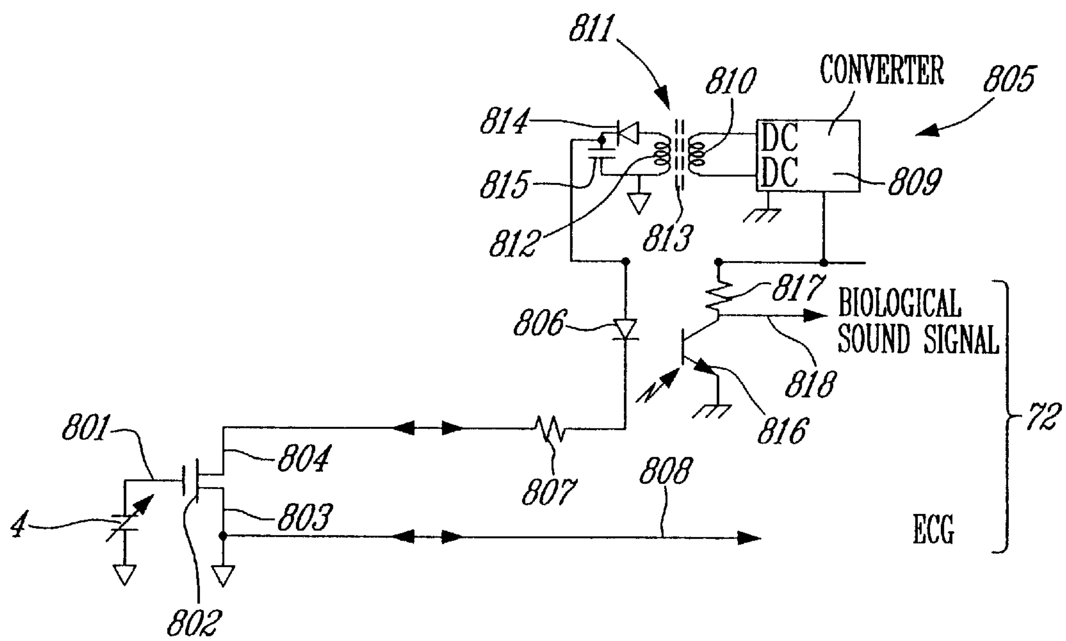
FIG. 9 is the circuit of an illustrative embodiment of piezoelectric sound monitor capable of producing both a biological sound signal and an ECG signal.

FIG. 9 is the circuit of a second group of electronic components that can be implemented on the PCB 8.

The electric signal from the piezoelectric membrane 4 is applied to the gate electrode 801 of a FET transistor 802. The source electrode 803 of the transistor 802 constitutes an output 808 for an ECG signal.

The drain electrode 804 of the transistor 802 is supplied from a supply circuit 805 through a photodiode 806 and a biasing resistor 807. Supply circuit 805 comprises a DC—DC converter 809 supplying a DC voltage and current to a primary winding 810 of an insulating transformer 811. The current through the primary winding 810 induces a DC voltage and current across a secondary winding 812 through an armature 813 of the insulating transformer 811. DC current is supplied from the secondary winding 812 of the insulating transformer 811 to the photodiode 806, the resistor 807 and the drain electrode 804 of the FET transistor 802 through a rectifying diode 814 and a filtering capacitor 815.

DC voltage and current from the converter 809 is also supplied to the collector of a phototransistor 816 through a biasing resistor 817. The emitter of the phototransistor 816 is grounded. As illustrated in FIG. 9, the collector of phototransistor 816 constitutes an output 818 for a biological sound signal.

In operation, the current through the source electrode 803 of the FET transistor 802 is modulated by the electric signal from the piezoelectric membrane 4. This current produces on the output 808 an ECG signal.

The current through the photodiode 806, resistor 807 and drain electrode 804 is also modulated by the electric signal from the piezoelectric membrane 4 that is applied to the gate electrode 801 of the FET transistor 802. In response to this modulated current, the photodiode 806 produces modulated light applied to the phototransistor 816 to produce on the output 818 an output biological sound signal.

Both the signals on the outputs 808 and 818 are transmitted through the two individually insulated conductors of the cable 72 to an external detector circuit (not shown).

Figure 10:
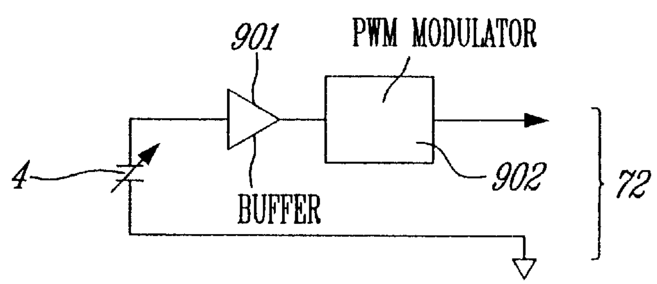
FIG. 10 is the circuit of an illustrative embodiment of piezoelectric sound monitor including a piezoelectric membrane, a buffer, and a PWM modulator.

FIG. 10 is the circuit of a third group of electronic components that can be implemented on the PCB 8. The electric signal produced by the piezoelectric membrane 4 is applied to a buffer 901 before being PWM (Pulse Width Modulation) modulated in modulator 902. The PWM modulated signal from the PWM modulator 902 is finally transmitted through the cable 72.

As illustrated in FIG. 6, the connector 56 includes a housing 67 made, for example, of electrically insulating molded plastic material. The housing 67 encloses three bent, electrically conductive spring blades such as 70 for contacting the three laterally adjacent electrically conductive traces 96 of the PCB 8. The spring blades 70 are also electrically connected to the conductors of the multi-conductor cable 72.

Figure 7:
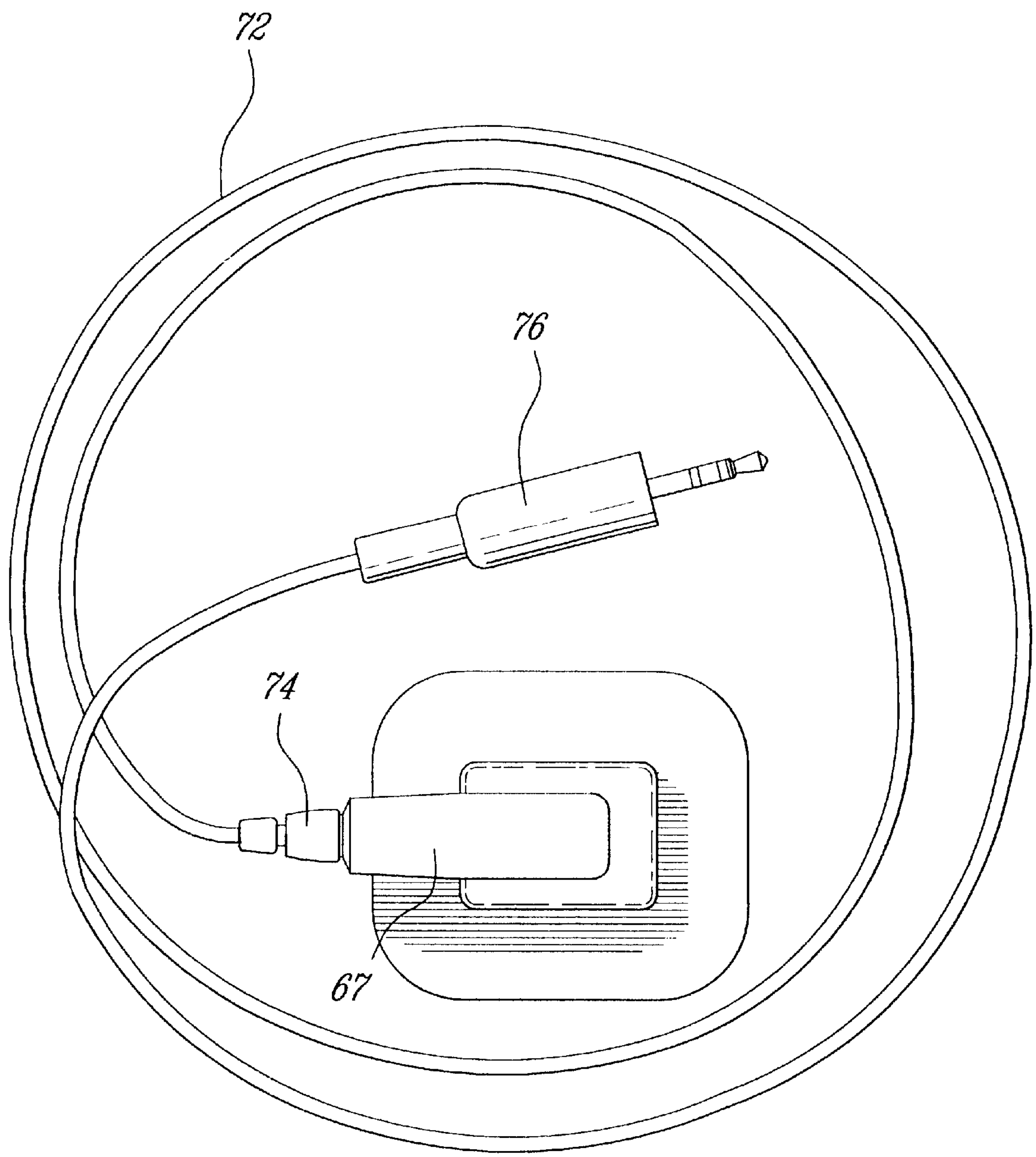
FIG. 7 is a top plan view of the assembly including the piezoelectric sound monitor of FIG. 3, the external connector of FIG. 3, and a cable extending from the connector according to an illustrative embodiment of the present invention.

In the illustrative embodiment, the multi-conductor cable 72 consists of a pair of stranded, individually insulated electric conductors (not shown). This pair of conductors is wrapped in a braided electrically conductive shield which, in turn, is encased in an electrically insulating jacket. Referring to FIG. 6, a pliable plastic cuff 74 is mounted on the cable 72 adjacent the housing 67 so as to improve the durabilty of the cable 72. Another connector such as 76 (FIG. 7) can be mounted on the distal end of the multi-conductor cable 72 for attachment to an external detector device.

Referring back to FIG. 4, the housing 67 comprises an outer U-shaped groove (track) 88 for sliding on the U-shaped track 92 of the housing 10 until the spring blades 70 of the connector 56 slide on and contact the respective electrically conductive traces 96 of the PCB 8. The spring blades 70 exert a downward pressure on the respective, electrically conductive traces 96 to ensure reliable contact. An interesting characteristic of the connector 56 is that the spring blades 70 remain connected to the electrically conductive traces 96 even when the groove 88 is, to some extent, partially removed from the track 92.

The fit between the groove 88 and the track 92 is such that the connector 56 is held firmly within the window 58.

Still referring to FIG. 4, the housing 67 of the connector 56 comprises upper 78 and lower 86 housing portions. The proximal ends of the spring blades 70 are mechanically secured, for example soldered to an elongated and rectangular PCB 80. As illustrated, PCB 80 is enclosed within an inner space delimited between the upper 778 and lower 86 housing portions. From the PCB 80, the spring blades 70 are bent and guided within respective parallel, laterally adjacent and vertically extending slots such as 82 of the lower housing portion 86. As shown in FIG. 6, the spring blades 70 comprise respective arcuate portions extending from the underside of the lower housing portion 86 to contact the traces 96.

Finally both the spring blades and the electrical conductors of the cable 72 are connected to the printed circuit of the PCB 80. In fact, the printed circuit of the PCB 80 electrically connects to the conductors of the cable 72 the spring blades 70 and the traces 96 when in contact with the blades 70.

Although the present invention has been described hereinabove with reference to an illustrative embodiment thereof, this embodiment can be modified at will, within the scope of the appended claims, without departing from the spirit and nature of the present invention.

What is claimed is:

1. A piezoelectric sound monitor, comprising:

a piezoelectric membrane including an inner face, an outer face, and first and second peripheral portions; and a piezoelectric membrane support structure including:

an outer face, the inner face of the piezoelectric membrane being applied to the outer face of the support structure;

two first mutually facing membrane-clamping walls, the first peripheral portion of the piezoelectric membrane being clamped between the two first walls;

a first electrically conductive area located on one of the two first walls for electrically contacting the inner face of the piezoelectric membrane;

two second mutually facing membrane-clamping walls, the second peripheral portion of the piezoelectric membrane being clamped between the two second walls; and a second electrically conductive area located on one of the two second walls for electrically contacting the outer face of the piezoelectric membrane.

2. A piezoelectric sound monitor, comprising:

a frame defining a window and having first and second faces;

a piezoelectric membrane extending across the window of the frame and including an outer face, an inner face applied to the first face of the frame, and first and second generally opposite peripheral portions;

a board having a first face toward the second face of the frame, a second face opposite to the first face, a first electrically conductive area on the first face of the board, and a second electrically conductive area on the second face of the board; and a housing connected to the frame and having an inner face toward the second face of the board;

wherein:

the first peripheral portion of the piezoelectric membrane is bent over the second face of the frame and clamped between the second face of the frame and the first electrically conductive area whereby the first electrically conductive area is in electrical contact with the outer face of the piezoelectric membrane; and the second peripheral portion of the piezoelectric membrane is bent over the second face of the board and is clamped between the second electrically conductive area and the inner face of the housing whereby the second electrically conductive area is in electrical contact with the inner face of the piezoelectric membrane.

3. A piezoelectric sound monitor as defined in claim 2, wherein the piezoelectric membrane comprises a sheet core of piezoelectric material, a first electrode coating forming the outer face of the piezoelectric membrane, and a second electrode coating forming the inner face of the piezoelectric membrane.

4. A piezoelectric sound monitor as defined in claim 2, wherein:

the frame is hollowed out to form a seat for receiving the board; and the housing defines a shallow cavity to receive the frame, the piezoelectric membrane and the board.

5. A piezoelectric sound monitor as defined in claim 2, further comprising a self-adhesive member comprising a self-adhesive face for adhering the piezoelectric sound monitor to a patient's body with the outer face of the piezoelectric membrane applied to said patient's body in order to sense biological sounds produced within the patient's body.

6. A piezoelectric sound monitor as defined in claim 5, wherein said self-adhesive member comprises a self-adhesive sheet clamped between the board and frame of the piezoelectric sound monitor.

7. A piezoelectric sound monitor as defined in claim 2, wherein the board is a printed circuit board, and wherein the first and second electrically conductive areas are connected to a printed circuit of said printed circuit board.

8. A piezoelectric sound monitor as defined in claim 2, further comprising mutually mating pairs of pin and hole for connecting the housing to the frame.

9. A piezoelectric sound monitor as defined in claim 7, wherein the second face of the printed circuit board comprises electrically conductive traces for connection to an external connector, the electrically conductive traces being connected to the printed circuit of the printed circuit board.

10. A piezoelectric sound monitor as defined in claim 9, wherein the housing comprises an opening for exposing the electrically conductive traces.

11. A piezoelectric sound monitor as defined in claim 10, wherein the external connector includes a housing, and wherein the housing of the external connector and the housing of the piezoelectric sound monitor comprise complementary track elements sliding in each other.

12. A piezoelectric sound monitor as defined in claim 11, wherein the electrically conductive traces are linear, parallel and laterally adjacent to each other, and parallel to a direction of sliding of the track elements in each other, whereby blades of the external connector slide on the laterally adjacent traces when the tracks elements slide in each other.

13. A piezoelectric sound monitor as defined in claim 10, wherein the opening of the housing defines a track for receiving the external connector.

14. A piezoelectric sound monitor as defined in claim 7, further comprising at least one electronic component connected to the printed circuit of the printed circuit board for processing an electric signal produced by the piezoelectric membrane in response to detection of a sound.

15. A piezoelectric sound monitor as defined in claim 14, wherein said at least one electronic component comprises a FM modulator supplied with the electric signal produced by the piezoelectric membrane.

16. A piezoelectric sound monitor as defined in claim 14, wherein said at least one electronic component comprises a PWM modulator supplied with the electric signal produced by the piezoelectric membrane.

17. A piezoelectric sound monitor as defined in claim 16, wherein said at least one electronic component further comprises a buffer for preprocessing the electric signal supplied from the piezoelectric membrane to the PWM modulator.

18. A piezoelectric sound monitor as defined in claim 7, further comprising at least one electronic component connected to the printed circuit of the printed circuit board for producing a biological sound signal and an ECG signal from an electric signal produced by the piezoelectric membrane in response to detection of a biological sound.

19. A piezoelectric sound monitor as defined in claim 18, wherein said at least one electronic component comprises a FET transistor having a gate electrode supplied with the electric signal produced by the piezoelectric membrane, a source electrode for supplying the ECG signal and a drain electrode for supplying the biological sound signal.

20. A piezoelectric sound monitor as defined in claim 18, wherein said at least one electronic component further comprises an optical coupler for transmitting the biological sound signal from the drain electrode of the FET transistor.

21. A method for fabricating a sound monitor for the detection of sounds, comprising:

clamping a first peripheral portion of a piezoelectric membrane to a first contact area such that a first face of the piezoelectric membrane is in contact with the first contact area;

spreading the piezoelectric membrane across a window of a frame; and clamping a second peripheral portion of the piezoelectric membrane to a second contact area such that a second surface of the piezoelectric membrane is in contact with the second contact area.

* * * * *